United States Patent [19]
Smith, Jr.

[11] Patent Number: 5,118,873
[45] Date of Patent: Jun. 2, 1992

[54] PROCESS FOR THE PREPARATION OF MTBE

[75] Inventor: Lawrence A. Smith, Jr., Houston, Tex.

[73] Assignee: Chemical Research & Licensing Company, Houston, Tex.

[21] Appl. No.: 615,326

[22] Filed: Nov. 19, 1990

[51] Int. Cl.⁵ .................... C07C 41/05; B01D 3/00
[52] U.S. Cl. .................... 568/697; 203/DIG. 6
[58] Field of Search .............. 203/DIG. 6; 568/697

[56] References Cited

U.S. PATENT DOCUMENTS

| | | | |
|---|---|---|---|
| 4,215,011 | 7/1980 | Smith, Jr. | 252/426 |
| 4,232,177 | 11/1980 | Smith, Jr. | 585/324 |
| 4,302,356 | 11/1981 | Smith, Jr. | 252/426 |
| 4,307,254 | 12/1981 | Smith, Jr. | 568/697 |
| 4,336,407 | 6/1982 | Smith, Jr. | 568/697 |
| 4,443,559 | 4/1984 | Smith, Jr. | 502/527 |
| 4,540,831 | 9/1985 | Briggs | 568/697 |

FOREIGN PATENT DOCUMENTS 929537 7/1973 Canada.
0008860 7/1978 European Pat. Off..

Primary Examiner—Marianne Cintins
Assistant Examiner—Rebecca Cook
Attorney, Agent, or Firm—Kenneth H. Johnson

[57] ABSTRACT

A process is provided for etherification of essentially pure $IC_4^=$ with MeOH to form MTBE in a distillation column reactor containing a fixed bed acid cation exchange resin as a catalytic distillation structure in an a distillation reaction zone. An inert $C_4$ hydrocarbon is initially fed to the distillation column reactor to act as a diluent and a heat sink which boils at the desired temperature range for the reaction. Additionally the inert $C_4$ diluent acts as an azeotroping agent for the MeOH in the lower end of the column carrying more of the MeOH back up into the reaction distillation zone. After start up and circulation the inert $C_4$ hydrocarbon feed is stopped and that in the system is retained therein by total reflux of the overheads and judicious operation of the lower portion of the distillation column reactor.

13 Claims, 2 Drawing Sheets

PROCESS FOR THE PREPARATION OF MTBE

BACKGROUND OF THE INVENTION

1. Field of the Invention

The present invention relates to the production of methyl tertiary butyl ether (MTBE) from the reaction of isobutylene ($iC_4=$) with methanol (MeOH). More particularly the invention relates to a process where high purity $iC_4=$ may be used as the feed while still maintaining adequate temperature control and $iC_4=$ selectivity to MTBE. Most particularly the invention relates to a catalytic distillation process wherein an inert $C_4$ hydrocarbon is initially fed to a distillation column reactor to provide a heat sink and dilute the reactants. After start up the initial feed of the inert $C_4$ hydrocarbon is ceased and that fed is retained in the system.

2. Related Art

The production of MTBE from the acid catalyzed reaction of $iC_4=$ and MeOH is well known in the art. Generally the $iC_4=$ is contained in a mixed hydrocarbon stream containing predominantly $C_4$'s which includes normal butenes, butanes and possibly lighter $C_3$ hydrocarbons. The $iC_4=$ content of these streams is typically from 10-70 mole %. The MeOH preferentially reacts with the $iC_4=$ to form MTBE with the remainder of the materials in the mixed hydrocarbon passing through essentially as inerts.

One major difficulty with the $iC_4=$/MeOH reaction has been temperature control due to the exothermicity of the reaction. Several methods of temperature control have been applied including indirect heat exchange in the catalyst bed, inter-bed cooling and quench. One method which has found wide spread acceptance is catalytic distillation wherein the heat of reaction simply causes boil up of the material in the catalyst bed. The temperature is controlled by the pressure. This particular method is exemplified by commonly owned U.S. Pat. Nos. 4,232,177; 4,307,254; and 4,336,407. A variation utilizing vaporization of the mixture for heat removal is disclosed in Canadian Pat. No. 929,537 wherein the vaporized portion is condensed and returned to the reactor, there being no distillation or separation. Additionally U.S. Pat. No. 4,540,831 discloses substantially the same process as the Canadian reference wherein all of the overheads are condensed and both products and unreacted materials are withdrawn as bottoms.

The catalytic distillation method of reaction works well when there is sufficient material within the bed to act as a heat sink-that is, there is sufficient material within the bed to absorb all of the heat of reaction without complete vaporization in the bed. After complete vaporization, the heat would simply be added as sensible heat and increase the temperature.

In U.S. Pat. No. 4,540,831 the broad embodiment of the process comprises exothermally reacting a first chemical compound and second chemical compound in a reaction zone to form a third chemical compound, vaporizing the first or second compound to remove heat and condensing the vapor overhead and removing the third compound and substantially all of the unreacted first and second compound in the bottoms effluent steam. The patent for example describes an MTBE process using as a feed an admixture of $C_4$ hydrocarbons including butanes and isobutylene in a process where the MTBE formed within the catalyst bed and the remaining $C_4$ hydrocarbons descend through the catalyst bed and are removed as a single combined effluent stream.

The use of concentrated $iC_4=$ as a feed stock for MTBE processes presents special problems because of the heat of reaction and the potential loss of selectivity due especially to dimerization. A simple solution to this problem would be to dilute the $iC_4=$ feed with inerts that boil in the reaction temperature range as the more common feed streams already are. The best diluents would therefore be other $C_4$'s, such as the butanes and normal butenes in the mixed hydrocarbon streams available.

However, these other $C_4$'s have value as feedstocks to other processes and while they are not appreciably consumed in the MTBE process, they do become contaminated, especially with MeOH and other oxygenated products which reduce their value as feedstocks as, for example HF alkylation. More significantly the dilution of a substantially pure isobutylene feed with sufficient inert diluents, e.g., 10 to 70% isobutane based on isobutylene, results in the processing of large quantities of materials to separate them from the product. Thus, by dilution, a pure reactant feed is contaminated to dampen the reaction and removed to get the product, which requires larger equipment.

SUMMARY OF THE INVENTION

Briefly the present invention is a process for etherification of substantially pure $iC_4=$ with MeOH to form MTBE in a distillation column reactor containing a fixed bed acid cation exchange resin as a catalytic distillation structure in a distillation reaction zone. An inert $C_4$ hydrocarbon is initially fed to the distillation column reactor to act as a diluent and a heat sink which boils at the desired temperature range for the reaction. Additionally the inert $C_4$ diluent acts as an azeotroping agent for the MeOH in the lower end of the column carrying more of the MeOH back up into the reaction distillation zone. After start up and circulation the inert $C_4$ hydrocarbon feed is stopped and that in the system is retained therein by total reflux of the overheads and judicious operation of the lower portion of the distillation column reactor. Thus forming an isobutane blanket in the reactor. Very little, if any, of the inert $C_4$ hydrocarbon is taken as bottoms which primarily consists of the MTBE product and some unreacted MeOH. Some of the overheads may have to be withdrawn as a bleed stream to remove the lighter hydrocarbons which may be contained in the inert stream and for pressure control of the distillation column reactor. Preferably the mole ratio of isobutylene to isobutane maintained in the catalyst zone is in the range of about 1:5 to 1:100; preferably 1:10 to 1:50. Make up inert $C_4$ hydrocarbon is added only to replace the small amount in the bottoms and the overhead bleed.

DESCRIPTION OF THE PREFERRED EMBODIMENTS

Figure 1:
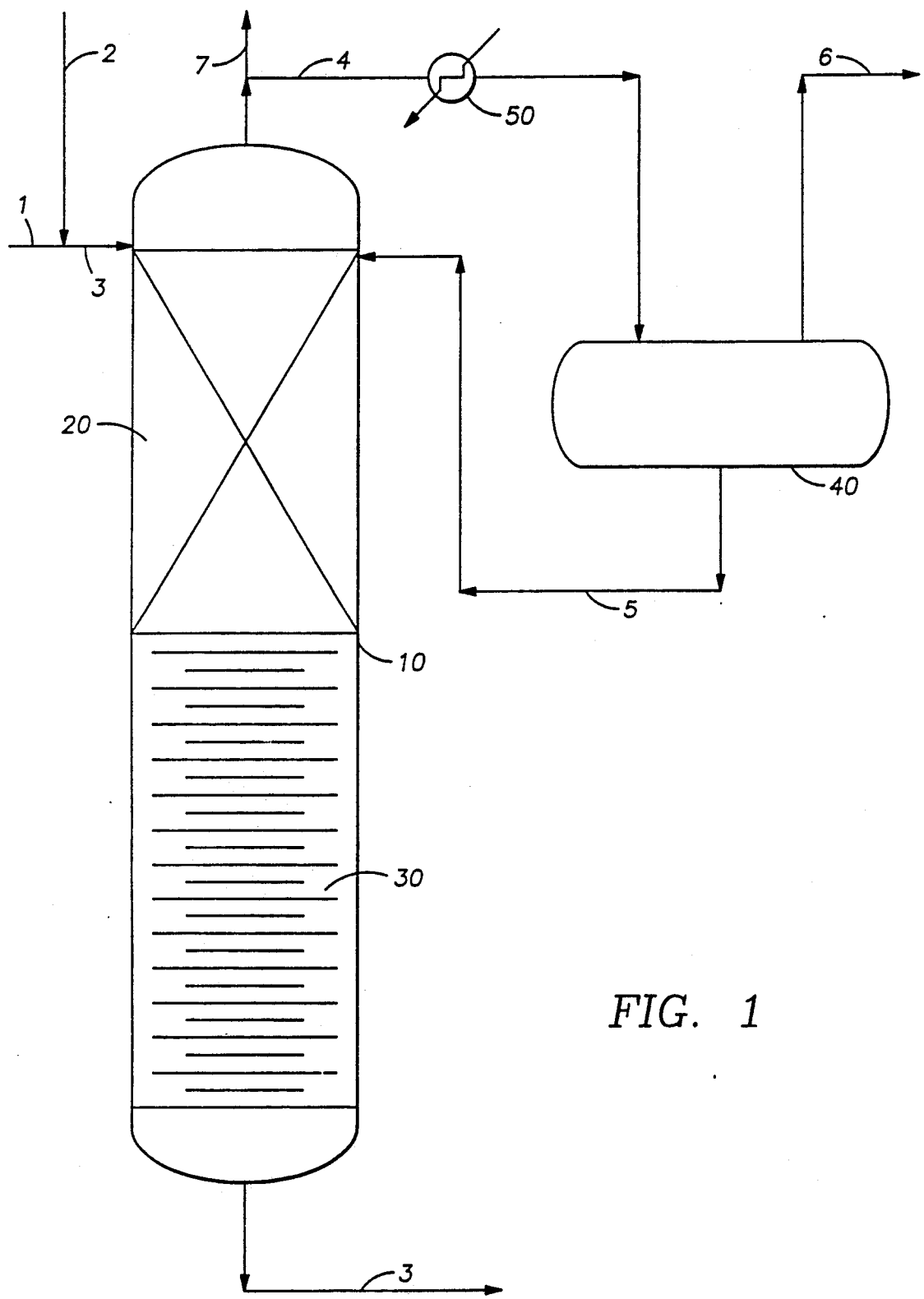
FIG. 1 is a flow diagram in schematic form of one embodiment of the present invention.

A catalytic distillation process utilizes a distillation column reactor which contains one or more distillation zones and one or more reaction distillation zones. The zones are distinct because the distillation zones contain standard distillation structure such as inert packing or distillation trays. The reaction distillation zone contains a catalytic distillation structure which acts both as a catalyst for the reaction and a distillation structure for the fractional distillation of the mixture within the reaction distillation zone.

Catalyst suitable for the MeOH/iC$_4^=$ reaction to produce MTBE are cation exchange resins, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethyl benzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenyl ether and others. The polymers may be prepared in the presence or absence or solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfuric acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0 to 150. C and the sulfuric acid should contain sufficient sulfur trioxide after the reaction. The resulting products preferably contain an average of 1.3 to 1.8 sulfonic acid groups per aromatic nucleus. Particularly suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example German Patent Specification No. 908,247).

The ion exchange resin is preferably used in a granular size of about 0.25 to 1 mm, although particles from 0.15 mm up to about 1 mm may be employed. The finer catalyst provide high surface area, but also result in high pressure drops through the reactor. The macroreticular form of these catalysts is preferred because of the much larger surface area exposed and the limited swelling which all of these resins undergo in a nonaqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. Nos. 3,784,399; 3,770,567 and 3,849,243.

In the preferred form the resin catalyst beads form too compact a bed and will not function adequately in a distillation, since there is a very large pressure drop through the bed and free flow of internal reflux and rising vapor is impeded. The resins may be used in the shape of conventional distillations structures, such as rings, saddles and the like. The particulate resins may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material to make the container is such that the catalyst is retained therein and will not pass through the openings in the material. Particles of about 0.15 mm size or powders may be used and particles up to about to about ¼ inch diameter may be employed in the containers. Containers and systems for using the particulate catalyst are variously described in commonly owned U.S. Pat. Nos. 4,215,011; 4,302,356 and 4,443,559 which are hereby incorporated by reference.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire, or expanded aluminum. Other resilient components may be similar open mesh knitted polymeric filament of nylon, teflon or the like. Other material, e.g., reticulated polyurethane foam (rigid or resilient) may be formed in place or applied around the catalyst component. In the case of larger catalyst components such from about ¼ to ½ inch pellets, spheres, pills and the like each such larger component may be individually intimately associated with or surrounded by the spacing component as described above. It is not essential that the spacing component entirely cover the catalyst component. It is only necessary that the spacing component intimately associated with the catalyst component will act to space the various catalyst components away from one another a described above. Thus, the spacing component provides in effect a matrix of substantially open space in which the catalyst components are randomly but substantially evenly distributed.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. The allows the requisite flows and prevents loss of catalyst. The cloth may be any material which is inert in the reaction. Fiber glass cloth or "Teflon" cloth are preferred.

In the following examples the catalyst section was packed with Purolite CT-175 resin packaged in individual bags each wrapped with demister wire. The wire mesh provides the support for the catalyst bags and provides some degree of vapor passage through the catalyst particles, which otherwise form a very compact bed which has a high pressure drop. The down flowing liquid is in intimate contact with the rising vapors in the column.

The distillation column reactor was operated in the "froth mode". That is, the column was operated at near flooding conditions such that the column was filled with a frothing liquid caused by the rising vapors through a liquid level maintained in the column. This insures complete wetting of the catalyst while still allowing for fractional distillation. The column is not "flooded" in the conventional sense by vapor flow, but rather by a downward liquid flow restricter to maintain a desired differential pressure which is expressed as a percent of differential pressure at flooded conditions, dP%.

Two embodiments are depicted in the attached figures in which like components are given like numerals for ease of reference. The figures are flow diagrams in schematic form and such conventional equipment as reboilers, controllers, and control valves are not included as they would be obvious to those of ordinary skill in the art of distillation column design.

Referring first to FIG. 1 the first embodiment is shown. The distillation column reactor 10 is shown to have the catalytic distillation structure in the upper portion of the column in a reaction distillation zone 20 and standard distillation structure in the lower portion of the column in the distillation zone 30. Essentially pure $iC_4=$ and MeOH are fed via line 1 and combined with the inert $C_4$ hydrocarbon stream from line 2 into feed line 3 which enters above the reaction distillation zone 30.

The MeOH and $iC_4=$ are contacted in the presence of the acid cation exchange resin in the reaction distillation zone 20 to form MTBE. The exothermic heat of reaction causes the resultant mixture in the reaction distillation zone 20 to boil. The MTBE being higher boiling than either the MeOH or $C_4$'s is distilled downward into distillation zone 30 where dissolved $C_4$'s and MeOH are distilled back up into the reaction distillation zone 20. The process of the present invention is preferably carried out at pressure in said distillation column reactor in the range of 100 to 200 psig and temperature in the range of 120 to 180° F. Substantially all of the $iC_4=$ reacts with MeOH in the reaction distillation zone 20. The amount of unreacted MeOH depends upon the molar ratio of MeOH to $iC_4=$, but if fed in a stoichiometric amount, substantially all of the MeOH should also be reacted. Recommended ratios of MeOH to $iC_4=$ are between 1:1 to 1.5:1.

The remainder of the $C_4$'s, predominantly the inert $C_4$ hydrocarbon, are carried overhead via line 4 and thence to condenser 50 where all of the condensibles (C4+) are condensed and collected in receiver/separator 40. Substantially all noncondensible material, such as any $C_3$ and lighter hydrocarbon contained in the inert $C_4$ hydrocarbon stream, are vented via line 6. A small bleed stream 7 is provided in the over head vapor line 3 for pressure control. All of the condensed material in the receiver 40 are returned to the top of the column as reflux. Once reflux has been established make up inert $C_4$ hydrocarbon is added only as required to replenish that lost in bleed 7. Essentially pure MTBE is withdrawn from the distillation column reactor as bottoms via line 3.

Essentially all of the $iC_4=$ will be consumed in the reaction distillation zone 20. Therefore very little is taken in the overheads 4 or dissolved in the product MTBE leaving the reaction distillation zone 20. Depending upon the molar ratio of MeOH to $iC_4=$ some MeOH will be dissolved in the MTBE and carried downward into the distillation zone 30. In such a case it might be desirable to divert some of the reflux (mostly inert $C_4$ hydrocarbon) to distillation zone 30 where it would act as an azeotroping agent for the MeOH and insure that all of the MeOH would be distilled back up into the reaction distillation zone 20.

Figure 2:
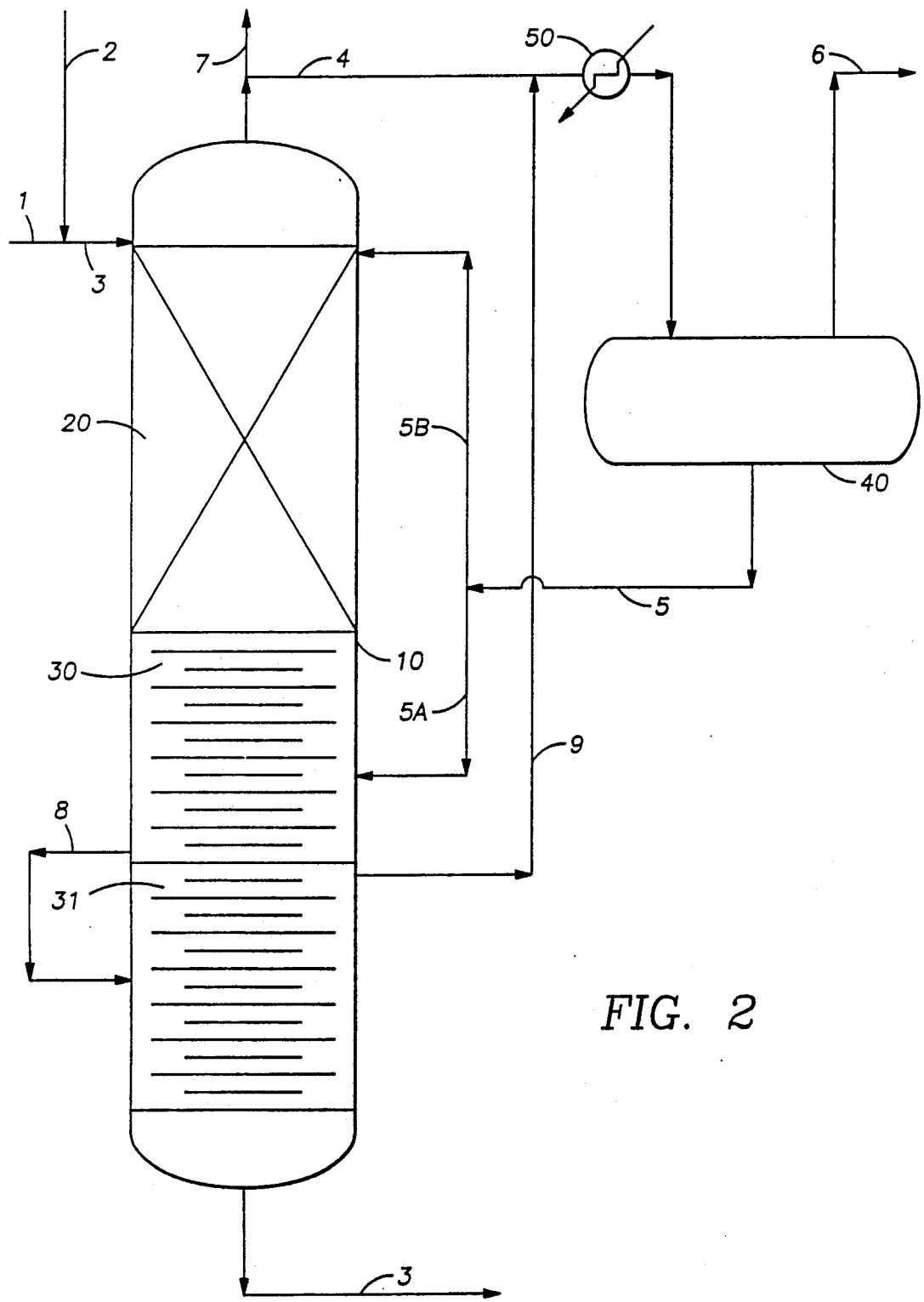
FIG. 2 is a flow diagram in schematic form of a second embodiment of the present invention.

A second embodiment of the process is shown in FIG. 2. This embodiment differs from the first in that a separate distillation section 31 is provided below the distillation zone 30 which might be in the form of a separate column. The liquid from distillation zone 30 is fed to the intermediate section of the separate section 31 via line 8 and a vapor containing predominantly inert $C_4$ hydrocarbon is taken from the top tray via line 9 and combined with the overheads in line 4 and condensed therewith by condenser 50 and collected in receiver 40. An additional feature of this embodiment is that part of the liquid $C_4$'s from the receiver 40 is diverted via line 5A to the lower distillation zone 30 as an azeotroping agent for the MeOH as discussed above. The remainder of the $C_4$'s are refluxed to the top of the column via line 5B.

While both embodiments have been directed to using 100% $iC_4=$ feed, the process should lend itself to processes which use $iC_4=$ streams containing high enough purity (i.e. 60-100%) to cause the temperature control problems. That is, sufficient diluent in the form of inert $C_4$ hydrocarbon may be initially added as desired to control the temperature and selectivity, and that added retained in the system by the method. This would reduce the amount of diluent necessary and reduce the problems of removing contaminants in the diluent.

EXAMPLES

The following examples were run using a one inch laboratory column twenty feet in height. The top six feet were packed with Purolite CT-175 resin contained in individual fiber glass bags and wrapped with demister wire. The weight of dry catalyst was 50 grams. The lower sixteen feet of the column was packed with inert ceramic saddles. Thermocouple probes were placed in the column with probes 11 through 14 (numbering from the bottom up) in the catalyst bed.

Analysis was by gas chromatography with FID detectors. The columns were capillary SE-30 with subambient temperature programming, and Carbowax 20M. Samples were taken in sample bombs and injected through a suitable sampling valve the gas chromatograph.

When operating in the froth mode there is so much material in the column that a substantial amount of time is required to reach a new steady state. Samples were taken ever three hours until sequential samples had essentially the same analysis.

Example 1 (comparative)

Three runs were made to determine the effect of $iC_4=$ concentration using isobutane as a diluent of the $iC_4=$ stream. The $iC_4=$ concentration in the first run was 35 mole %, 45 mole % in the second and 50 mole % in the third. The results are shown in Table I. The feed to the laboratory column in the first two runs was below the catalyst bed. At a feed $iC_4=$ concentration of 45 mole % the selectivity to MTBE fell off rapidly. It did not appear feasible to feed below the bed because insufficient MeOH is carried up into the catalyst by the relatively small amount of hydrocarbon present. Even with a large excess of MeOH (Run 2), the selectivity decreased for the 45 mole % feed as compared to the 35 mole % feed. The feed for the third run was moved to above the catalyst bed to insure that all of the MeOH contacted the catalyst and the selectivity was regained.

TABLE I

| Run. no. | 1 | 2 | 3 |
|---|---|---|---|
| $iC_4^=$ Feed | 35% | 45% | 50% |
| Pressure, psig | 140 | 124 | 140 |
| Cat Zone dP, % | 73 | 82 | 74 |
| Feed Point | Below cat. | Below cat. | Above cat. |
| Temperature, °F. | | | |
| Bottoms | 313 | 274 | 227 |
| Catalyst | 157 | 153 | 129 |
| Overhead | 154 | 140 | 124 |
| Feed Rate, g/hr | 548.8 | 912 | 545 |
| MeOH/$iC_4^=$ mole ratio | 1.06 | 1.4 | 1.1 |
| Bottoms, g/hr | 176 | 531 | 330 |
| Bottoms analysis, wt % | | | |
| Lt. ends | 0.001 | 0.014 | 0.000 |
| $C_4$'s | 0.052 | 0.039 | 21.995 |
| MeOH | 1.961 | 7.174 | 4.340 |
| TBA | 0.280 | 0.338 | 0.252 |
| MTBE | 97.469 | 82.332 | 73.390 |
| Unk. | 0.001 | 0.001 | 0.000 |
| DIB-1 | 0.168 | 7.188 | 0.007 |
| DIB-2 | 0.049 | 2.126 | 0.002 |
| Hvys | 0.020 | 0.798 | 0.000 |
| MTBE production rate, g/hr/g cat. | 3.43 | 4.37 | 4.84 |
| MTBE purity, wt % (excl lt ends and $C_4$'s) | 99.47 | 88.73 | 99.64 |
| Conv. of $IC_4^=$ to MTBE, % | 68.57 | 63.86 | 74.32 |

Example 2

Two runs were made using a blanket of isobutane in the upper portion of the column. The tower was started up to reflux with isobutane and the $IC_4^=$/MeOH was fed above the catalyst zone. The differential pressure in the froth mode was maintained (with a constant heat input) by the feed rate balanced by the bottoms withdrawal rate. The amount of isobutane necessary as a blanket in the catalyst zone to accommodate the heat of reaction was controlled by the position of a temperature break between the bottoms and the catalyst zone. The position was held constant by occasional or continuous addition of the inert hydrocarbon. Results are given in Table II.

Excellent temperature control was possible using an isobutane blanket in the catalyst zone to moderate the reaction of 100% $iC_4^=$ feed with 10% excess MeOH (Run 4). However, using less than stoichiometric amounts of MeOH allowed the loss of some selectivity to MTBE (Run 5).

While there was still MeOH in the bottoms sample, the bottoms contained less than 2% total $C_4$'s. Better results should be achieved with a more efficient column. Hydrocarbon in the effluent, in the case of pure $iC_4^=$ feed, could be eliminated by distillation below the catalyst bed. The use of an analytical instrument to indicate MeOH concentration continuously should allow a minimum of MeOH to be withdrawn with the MTBE by adjusting the feed of MeOH to a minimum. A higher concentration of isobutane should help selectivity by increasing the azeotropic amount of MeOH distilling back into the catalyst zone.

TABLE II

| Run. no. | 4 | 5 |
|---|---|---|
| $iC_4^=$ Feed % | 100 | 100 |
| Pressure, psig | 115 | 105 |
| Cat Zone dP, % | 95 | 73 |
| Feed Point | Above cat. | Above cat. |
| Temperature, °F. | | |
| Bottoms | 251 | 264 |
| Catalyst | 155 | 155 |
| Overhead | 133 | 124 |
| Feed Rate, g/hr | 363 | 454 |
| MeOH/$iC_4^=$ mole ratio | 1.1 | 0.95 |
| Bottoms, g/hr | 245 | 316 |
| Bottoms analysis, wt % | | |
| Lt. ends | 0.025 | 0.005 |
| $C_4$'s | 1.418 | 1.930 |
| MeOH | 9.226 | 6.620 |
| TBA | 0.390 | 0.283 |
| MTBE | 85.332 | 88.536 |
| Unk. | 0.002 | 0.000 |
| DIB-1 | 0.197 | 1.845 |
| DIB-2 | 0.032 | 0.246 |
| Hvys | 0.113 | 0.246 |
| MTBE production rate, g/hr/g cat. | 4.18 | 5.60 |
| MTBE purity, wt % (excl lt ends and $C_4$'s) | 99.25 | 96.82 |
| Conv. of $iC_4^=$ to MTBE, % | 59.55 | 60.57 |
| Effective dilution ratio in Reactor isobutene/isobutane[1] | 2/100 | 10/100 |

[1]estimate

The invention claimed is:

1. A process for the production of methyl tertiary butyl ether from a substantially pure stream of isobutylene, comprising:
    (a) feeding a first stream comprising an inert $C_4$ hydrocarbon to a distillation column reactor into a feed zone;
    (b) after reflux of the first stream has been established terminating said first stream and concurrently feeding a second stream comprising substantially pure isobutylene and a third stream comprising methanol to said distillation column reactor into said feed zone;
    (c) concurrently in said distillation column reactor:
        (i) contacting said isobutylene with said methanol in a reaction distillation zone in the presence of an acid cation exchange resin in the form of a catalytic distillation structure thereby reacting a majority of said isobutylene with methanol to form methyl tertiary butyl ether, and
        (ii) fractionating the resultant mixture in said reaction distillation zone whereby unreacted methanol, unreacted isobutylene and inert $C_4$ hydrocarbons are recovered as overheads and methyl tertiary butyl ether, methanol and minor amounts of unreacted isobutylene and inert $C_4$ hydrocarbon are recovered as bottoms;
    (d) condensing substantially all of said overheads and returning substantially all of said condensed overheads to said distillation column as reflux; and
    (e) adding make up inert $C_4$ hydrocarbon from said first stream as necessary only to replace that incidentally removed.

2. The process according to claim 1 wherein a portion of said condensed overheads is diverted to a distillation zone below said reaction distillation zone.

3. The process according to claim 1 wherein a portion of said condensed overheads is fed to said distillation column reactor at a point below said reaction distillation zone.

4. The process according to claim 1 further comprising feeding the liquid bottoms from said distillation column to a separate distillation zone and combining the vapors from said second distillation zone with the overheads from said distillation column reactor.

5. The process according to claim 1 wherein a small bleed stream of said overheads is withdrawn to control the pressure in said distillation column reactor and said inert $C_4$ hydrocarbon is added to replace that removed in said bleed stream.

6. The process according to claim 1 wherein the molar ratio of methanol to isobutylene fed to said distillation column reactor is 1:1.

7. The process according to claim 1 wherein the molar ratio of methanol to isobutylene fed to said distillation column reactor is greater than 1:1.

8. The process according to claim 7 wherein the molar ratio of methanol to isobutylene fed to said distillation column reactor is 1.1:1.

9. The process according to claim 1 wherein said feed zone is above, said reaction distillation zone.

10. The process according to claim 1 wherein the combined concentration of unreacted isobutylene and inert $C_4$ hydrocarbon in said bottoms is less than 2 wt %.

11. The process according to claim 5 wherein said inert $C_4$ hydrocarbon stream contains small amounts of $C_3$ and lighter hydrocarbons and substantially all of said $C_3$ and lighter hydrocarbons are removed in said bleed stream.

12. The process according to claim 1 wherein the pressure in said distillation column reactor is in the range 100 to 200 psig.

13. The process according to claim 11 wherein the temperature in said reaction distillation zone is in the range of 120 to 180° F.

* * * * *